(12) United States Patent
Holden

(10) Patent No.: US 6,842,251 B1
(45) Date of Patent: Jan. 11, 2005

(54) CONFIGURABLE METROLOGY DEVICE THAT OPERATES IN REFLECTANCE MODE, TRANSMITTANCE MODE, OR MIXED MODE

(75) Inventor: James M. Holden, San Jose, CA (US)

(73) Assignee: Nanometrics Incorporated, Milpitas, CA (US)

( * ) Notice: Subject to any disclaimer, the term of this patent is extended or adjusted under 35 U.S.C. 154(b) by 340 days.

(21) Appl. No.: 09/923,723

(22) Filed: Aug. 6, 2001

(51) Int. Cl.$^7$ .......................... G01N 21/55; G01N 21/00
(52) U.S. Cl. ..................... 356/445; 356/73; 356/432
(58) Field of Search ................ 356/445–448, 356/630–632, 600–613, 432–436

(56) References Cited

U.S. PATENT DOCUMENTS

| | | | |
|---|---|---|---|
| 4,999,010 A | 3/1991 | Mattson et al. | 356/346 |
| 5,889,593 A | 3/1999 | Bareket | 356/445 |
| 6,075,612 A | 6/2000 | Mandella et al. | 356/445 |
| 6,084,662 A | 7/2000 | Seaburn | 356/73 |

FOREIGN PATENT DOCUMENTS

WO    WO 00/12961    3/2000

OTHER PUBLICATIONS

Gamsky, C. et al., "Quantitative analysis of chemically amplified negative photoresist using mirror–backed infrared reflection absorption spectroscopy" *SPIE vol. 2438*, pp. 143–152.

Gamsky, C., "Reflectance FT–1R For Monitoring Chemical Reactions In Chemically Amplified Photoresists For 0.25 μm X–Ray Lithography" UMI Dissertation Services, at the University of Wisconsin–Madison (1995), pp. 1–250.

Harrison, D. et al., "Innovations in Lithography Metrology for Characterization of Phase–Shift Mask Materials", *SPIE* (2001) pp. 233–240.

"n&k Analyzer 1512RT", downloaded Sep. 25, 2001 from <http://www.nandk.com/1512rt.html>, n&k Technology, Inc. (2001).

*Primary Examiner*—Gregory J. Toatley, Jr.
*Assistant Examiner*—Amanda Merlino
(74) *Attorney, Agent, or Firm*—Silcon Valley Patent Group LLP

(57) ABSTRACT

A metrology system includes a sample holder and a backside reflective element. The backside reflective element causes light that is transmitted through the sample to be reflected and transmitted a second time, in the opposite direction, through the sample. A variable collection range can be adjusted to place the sample, the reflective element or both within the collection range. The collection range is the range of focused light that will be detected. The system can be controlled to move one or both of the sample and the reflective element in or out of the collection range or to alter the optics to adjust the collection range so that one or both of the sample and reflective element are in the collection range. Thus, the metrology system can be configured to operate in reflectance mode, transmittance mode or a mixed reflectance/transmittance mode.

25 Claims, 5 Drawing Sheets

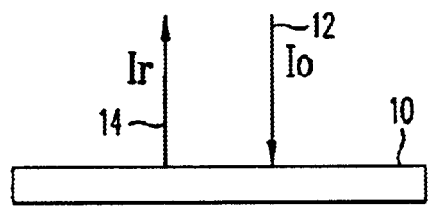
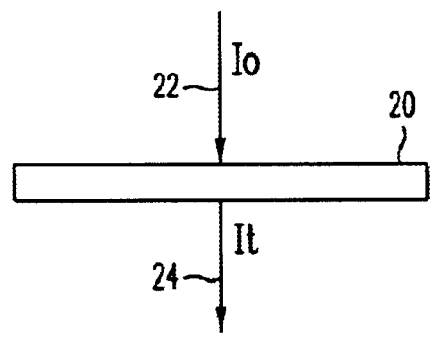
FIG. 1A (Prior Art)
FIG. 1B (Prior Art)
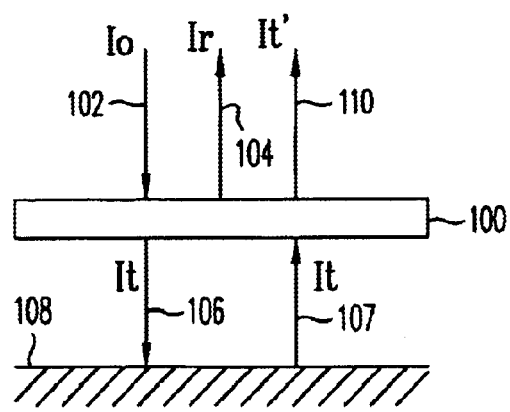
FIG. 2

CONFIGURABLE METROLOGY DEVICE THAT OPERATES IN REFLECTANCE MODE, TRANSMITTANCE MODE, OR MIXED MODE

FIELD OF THE INVENTION

The present invention relates to optical sampling of thin films and transparent substrates, and in particular to optical sampling using reflectance, transmittance and mixed modes.

BACKGROUND

Optical sampling of thin films is conventionally performed using either specular reflectance or transmittance. Conventionally, reflectance measurements and transmittance measurements are made separately. Specular reflectance measurements are based on the fraction of light intensity that is reflected from a sample surface. FIG. 1A shows a simplified schematic diagram of a conventional reflectance measurement of a sample 10. It should be understood that sample 10 typically includes one or more thin film layers (not shown). As shown in FIG. 1A, the sample 10 is exposed to a light beam 12 having an intensity Io. Part of the light beam 12 is reflected off sample 10 as light beam 14, which has an intensity Ir. The light beam 14 is collected with a detector (not shown). The reflectance, R, can then be measured as the ratio of the intensities of the reflected and incident light beams, as follows:

$$R = \frac{Ir}{Io}. \qquad \text{eq. 1}$$

The reflected intensity Ir of light beam 14 is less than the incident intensity Io of light beam 12 so that R<1.

Transmittance measurements are based on the fraction of light intensity that is lost as a beam passes through a sample. FIG. 1B shows a simplified schematic diagram of a conventional transmittance measurement of a sample 20. Again, it should be understood that sample 20 typically includes one or more thin film layers (not shown) that are to be measured. As shown in FIG. 1B, the sample 20 is exposed to a light beam 22 having an intensity Io. Part of the light beam 22 is transmitted through sample 20 as light beam 24, which has an intensity It. The transmitted light beam 24 is collected by a detector (not shown). The transmittance, T, can then be measured as the ratio of the intensities of the transmitted and incident light beams, as follows:

$$T = \frac{It}{Io}. \qquad \text{eq. 2}$$

As with reflectance, light intensity is lost upon transmittance so that the transmitted intensity It of light beam 24 is less than the incident intensity Io of light beam 22 so that T<1.

On example of transmittance measurement is found in a technique known as Mirror Backed Infrared Reflection Absorption Spectroscopy (MBIRRAS) that prescribes placing a mirror a fixed distance behind an absorbing film sample and which is described in "Reflectance FT-IR for monitoring chemical reactions in chemically amplified photoresist for 0.25 $\mu$m X-ray lithography", Christopher Gamsky, Ph.D. Dissertation, University of Wisconsin-Madison, 1995. The mirror and sample are spaced by a Teflon ring and held fixed by pressure from front and back plates. Incident light passes through the sample, reflects off the mirror and passes back through the sample. Measurements are explicitly performed at an oblique angle of incidence, e.g., 40° from normal, in order to avoid collecting light reflected from the surface of the sample. The air gap, which is the width of the Teflon ring, is selected to minimize interference fringes caused by collecting both the sample reflected and mirror reflected beams.

Typically, reflectance and transmittance measurements are preformed over some continuous range of wavelengths such as the mid-IR (400 cm$^{-1}$ to 4000 cm$^{-1}$). These spectra will normally contain features that become more or less pronounced as material properties, e.g., concentrations, change. It is therefore possible to correlate feature strength with these material properties and thereby measure these material properties. Typically, there is some range of the feature strength over which either reflectance or transmittance is usable and a single sample may contain some features within the range of a transmittance measurement and some features within the ranges of a reflectance measurement. In addition, some samples may have features that cannot be measured well by either reflectance or transmittance. In these cases it becomes necessary to modify the sample, such as the film thickness, for monitoring purposes—a modification that would be costly and require additional correlation to the originally unmeasurable sample.

Accordingly, what is needed is a metrology device that is easily configurable to operate in reflectance mode, transmittance mode or a mix of reflectance and transmittance mode.

SUMMARY

A metrology system, in accordance with the present invention, can be configured to operate in reflectance mode, transmittance mode or a mixed reflectance/transmittance mode. The metrology system includes a sample holder and a backside reflective element. The backside reflective element causes light that is transmitted through the sample to be reflected and transmitted a second time, in the opposite direction, through the sample. A variable collection range can be adjusted to place the sample, the reflective element or both within the collection range. The collection range is the range of focused light that will be detected. The system can be controlled to move one or both of the sample and the reflective element in or out of the collection range or to alter the optics to adjust the collection range so that one or both of the sample and reflective element are in the collection range.

Thus, in one aspect of the present invention, an apparatus for optically measuring characteristics of a sample includes a light source that produces a light beam along an optical path; a sample support for holding a sample within the optical path; and a reflective element within the optical path and downstream of the sample support. The apparatus also includes a means for positioning a sample held on the sample support, the reflective element, or both the sample held on the sample support and the reflective element within a collection range. The means for positioning may be, e.g., at least one actuator coupled to at least one of the sample support and the reflective element to move at least one of the sample support and the reflective element into and out of the collection range. Alternatively, the means for positioning may be, e.g., the optical elements that can adjust the collection range to include at least one of the sample and the reflective element in or out of the collection range. The apparatus also includes a light detector in the optical path, wherein the light detector receives light reflected from within the collection range.

In another aspect of the present invention, a method of measuring a characteristic of a sample includes producing a light beam to be incident on a sample; reflecting a portion of the light beam off the sample to form a reflected light beam; transmitting another portion of the light beam through the sample in a first general direction to form a transmitted light beam; reflecting the transmitted light beam back toward the sample; transmitting the transmitted light beam through the sample in a second general direction to form a second transmitted light beam, the second general direction being opposite the first general direction; configuring a collection range, the collection range being a range within which light is reflected; and detecting light reflected within the collection range. Configuring the collection range includes, e.g., moving at least one of the sample and a reflective element to a desired position in or out of the collection range, where the reflective element reflects the transmitted light beam back toward the sample. Alternatively, configuring the collection range includes, e.g., adjusting at least one optical element to alter the focus of the light beam between the sample and a reflective element that reflects the transmitted light beam back toward the sample; and adjusting at least one optical element to alter the focus of the light that is detected.

BRIEF DESCRIPTION OF THE DRAWINGS

FIG. 1A shows a simplified schematic diagram of a conventional reflectance measurement of a sample.

FIG. 1B shows a simplified schematic diagram of a conventional transmittance measurement of a sample.

FIG. 2 shows a simplified schematic diagram of measuring a sample using reflection and transmission of light in accordance with an embodiment of the present invention.

DETAILED DESCRIPTION

Figure 3:
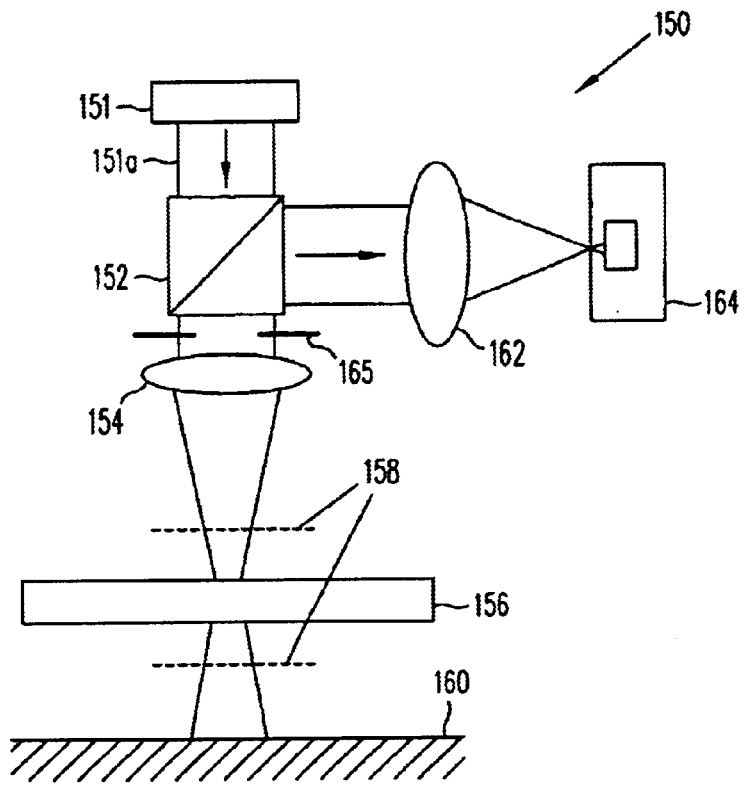
FIG. 3 shows a simplified schematic diagram of metrology device configured to operate in reflectance mode in accordance with an embodiment of the present invention.

FIG. 2 shows a simplified schematic diagram of measuring a sample 100 using reflection and transmission of light in accordance with an embodiment of the present invention. It should be understood that sample 100 can include one or more film layers, which are not shown in FIG. 2, and that sample 100 may be, for example, a silicon wafer or flat panel display or other such similar device.

As shown in FIG. 2, a light beam 102 having an intensity Io is incident on sample. Light beam 102 may be, for example, a beam of light from a FTIR spectrometer, such as the type manufactured by Midac Corp., in Irvine Calif. A portion of light beam 102 is reflected off sample 100, e.g., at the surface of sample 100 or at the interfaces of various overlying layers. The reflected light beam 104 has an intensity Ir.

Another portion of light beam 102 is transmitted through sample 100 resulting in transmitted light beam 106 having an intensity It. A mirror 108 is positioned beneath sample 100 such that the transmitted light beam 106 is reflected back towards sample 100 in the form of reflected transmitted light beam 107, as shown in FIG. 2. The mirror 108 should be highly reflective to the particular wavelengths of transmitted light beam 106. Thus, for example, if light beam 102 is an infrared light beam, mirror 108 should be coated with gold, which is highly reflective to infrared light. The reflected transmitted light beam 107 passes through sample 100 a second time, resulting in transmitted light beam 110 having an intensity of It'. Thus, light passes through sample 100 twice, thereby increasing sensitivity to properties associated with bulk light absorption.

It should be understood that while FIG. 2 shows light beams 102, 104, 106, 107, and 110 separated, these light beams may overlap, for example, if light beam 102 is normally incident on sample 100. Moreover, if light beam 102 is incident on sample 100 at an oblique angle, light beams 102, 104, 106, 107, and 110 will not overlap but reflected light beams, i.e., light beam 104 and light beam 107 will be reflected from the point of incidence on sample 100 (or the interface of any overlying layers) and mirror 108, respectively. Thus, the arrows in FIGS. 1 and 2 do not represent actual light rays, but rather the general direction of energy flow.

The light collected is the sum of the reflected light beam 104 with intensity Ir and the transmitted light beam 110 with intensity It'. The collected light can be written as a sum of ratios relative to the intensity of the incident light beam 102 resulting in a quantity S, as follows:

$$S = \frac{Ir}{Io} + \frac{It'}{Io} \qquad \text{eq. 3}$$

where the first term, Ir/Io, is the conventional reflectance and the second term, It'/Io, is the transmittance for a beam passing through sample 100, reflectance off mirror 108 and passing through sample 100 a second time. Thus, the quantity S contains both the reflectance and transmittance type information.

The combination of reflectance and transmittance type information in quantity S is advantageous because it permits the simultaneous measurement of sample properties that primarily affect measured reflectance and sample properties that primarily affect measured transmittance. In addition, the transmittance type measurement, It'/Io, is twice as sensitive to properties of the sample that affect transmittance, consequently, permitting higher precision measurements of samples with weaker absorption, such as those with lower concentrations, thin films and weak absorption cross-sections.

In an embodiment of the present invention, the quantity S can be modified as follows:

$$S = a \times \frac{Ir}{Io} + b \times \frac{It'}{Io} \qquad \text{eq. 4}$$

where "a" and "b" are changeable constants with 0<a<1 and 0<b<1. Thus, any particular measurement of the quantity S can be tailored to the particular sample of interest. For example, a sample with a low concentration of weakly absorbing species might require that the constant "a" is approximately 0 and the constant "b" is approximately 1 to emphasize the absorption term, while a sample with very strongly absorbing species might require working in reflectance such that "a" is approximately 1 and "b" is approximately 0. A sample between these two extremes might be most sensitively measured with both "a" and "b" in the middle of their ranges or by combining a sequence of reflectance/transmittance measurements in one measurement.

FIG. 3 shows a simplified schematic diagram of a metrology device 150 with sampling optics, shown as beam splitter 152 and objective lens 154 that measures the quantity S and that is configured to operate in reflectance mode, i.e., a≅1, b≅0, in accordance with an embodiment of the present invention. It should be understood that the beam splitter 152 and objective lens 154 are shown in FIG. 3 for exemplary purposes, and that beam splitter 152 and objective lens 154 may actually include any desired number of components and lenses. Moreover, the beam path of light shown in FIG. 3 is also exemplary and that any desired beam path may be followed.

As shown FIG. 3, metrology device 150 includes a light source 151 that produces a light beam 151a along an optical path. The light beam 151a is transmitted through beam splitter 152 and objective lens 154 and is incident on sample 156. A reflective element, e.g., mirror 160, is in the optical path downstream of the sample 156. Metrology device 150 also includes a collection lens 162 within the optical path and a detector 164. An aperture stop 165 is also disposed in the beam path. A collection range of the optics, which is indicated by broken lines 158, is a range in which any light reflected back toward detector 164 will be received. Light reflected back toward detector outside collection range 158 will not be detected. Thus, as shown in FIG. 3, light that is transmitted through sample 156 and reflected off mirror 160 will not be focused onto the light detector 164, causing the constant "b" in equation 4 to be approximately 0. However, light that is incident on sample 156 is within the collection range 158 and is therefore properly focused by objective lens 154 and collection lens 162 to be received by the light detector 164. Consequently, the constant "a" in equation 4 is approximately 1. The size of the collection range 158 can be adjusted by adjusting the numerical aperture of objective lens 154 and collection lens 162 through adjustment of the size of the aperture stop 165.

Figure 4:
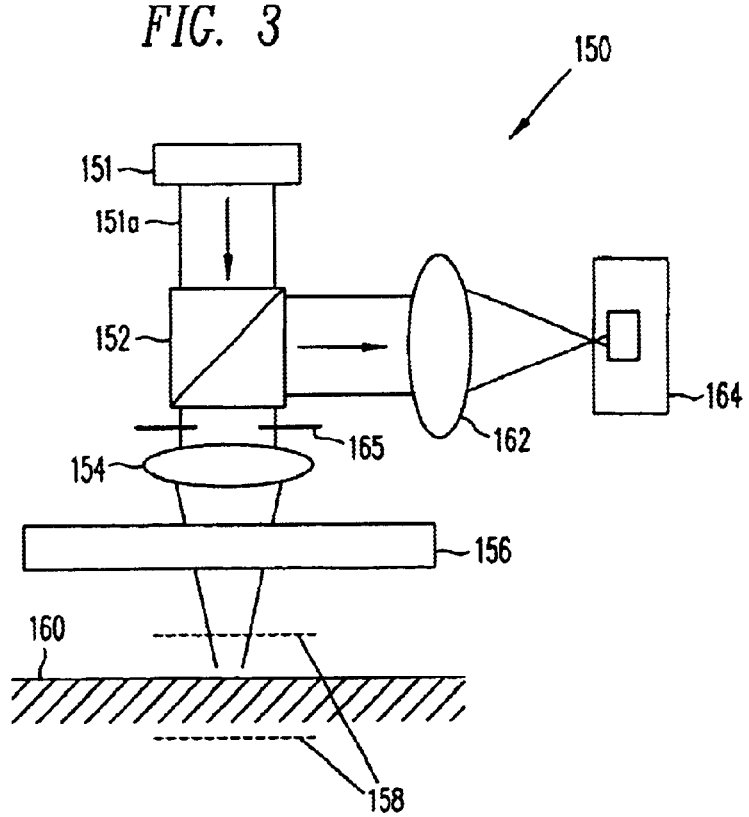
FIG. 4 shows a simplified schematic diagram of metrology device configured to operate in transmittance mode in accordance with an embodiment of the present invention.

FIG. 4 shows a simplified schematic diagram of metrology device 150 adjusted so that the mirror 160 falls within the collection range 158 of the optics. Consequently, metrology device 150 is operating in transmittance mode, i.e., a≅0, b≅1, in accordance with an embodiment of the present invention. As shown FIG. 4, because sample 156 is outside the collection range 158, light that is reflected from the surface of sample 156 will not be collected by the light detector, causing the constant "a" of equation 4 to be approximately 0. The light that is transmitted through sample 156, however, is reflected off mirror 160, which is within the collection range 158 of the optics. Thus, the light that is reflected off mirror 160 passes through sample 156 a second time, focused by objective lens 154 and is received by the light detector, causing the constant "b" of equation 4 to be approximately 1.

Figure 5:
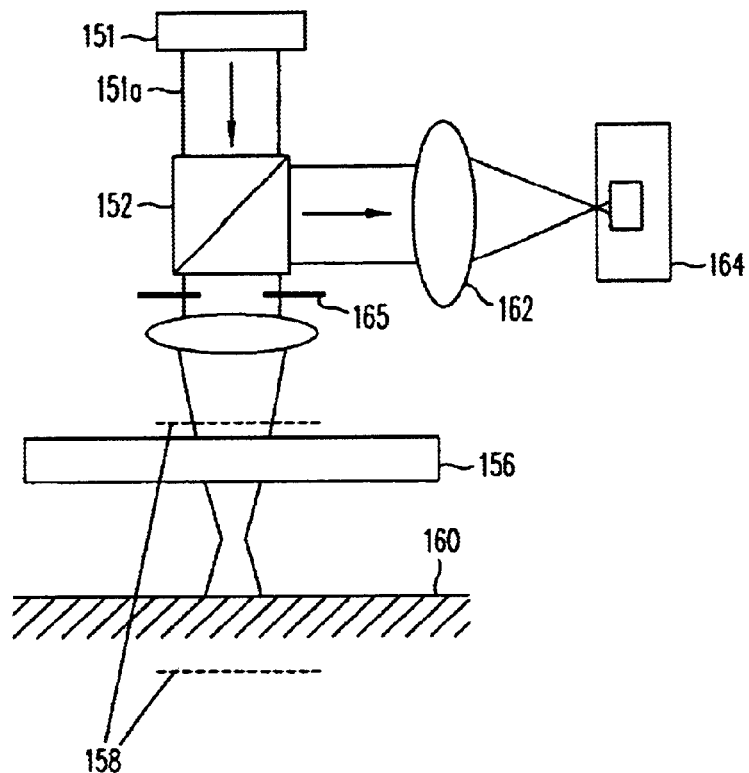
FIG. 5 shows a simplified schematic diagram of metrology device configured to operate in a combination of reflectance mode and transmittance mode in accordance with an embodiment of the present invention.

FIG. 5 shows a simplified schematic diagram of metrology device 150 adjusted so that both the mirror 160 and sample 156 fall within the collection range 158. Consequently, metrology device 150 is operating in a mixed mode, i.e., neither "a" nor "b" are approximately zero, in accordance with an embodiment of the present invention. Thus, light that is reflected from the sample 156 and the mirror 160 will be focused by objective lens 154 and collection lens 162 and will be received by the light detector 164. Thus, the constants "a" and "b" from equation 4 will both fall somewhere within their full ranges, i.e., between 0 and 1.

Figure 6A:
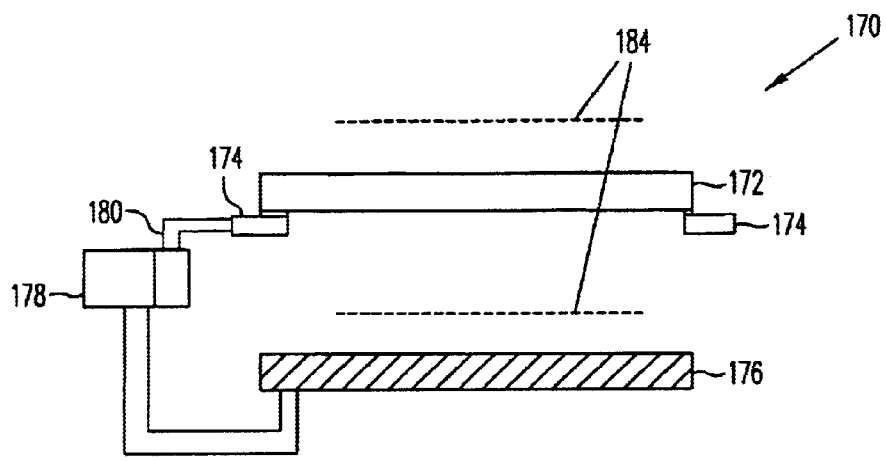
FIGS. 6A, 6B and 6C show simplified schematic diagrams of a metrology device with a sample mounted on a sample holder over a reflective element, where the metrology device is operating in reflectance mode, transmittance mode, and mixed mode, respectively.
Figure 6B:
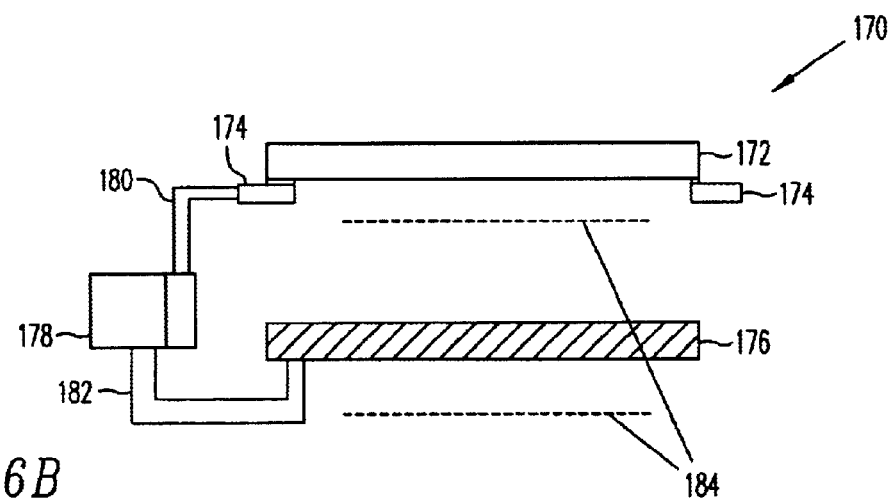
Figure 6C:
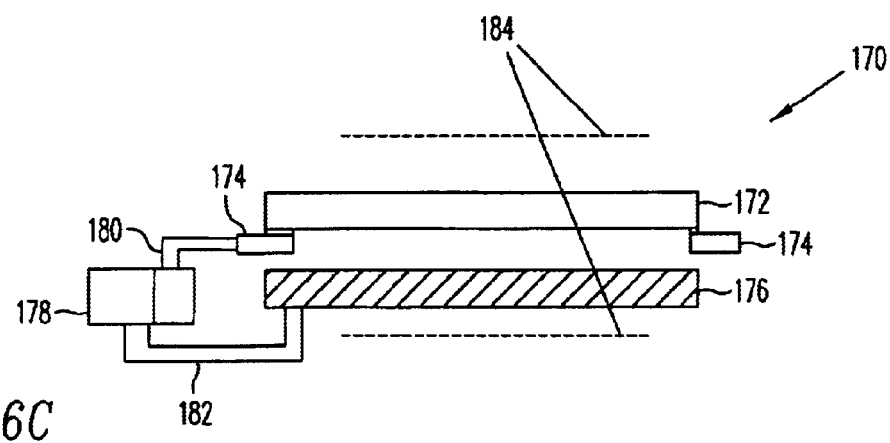

In one embodiment of the present invention, different modes of operation may be achieved by varying the spacing between the mirror and the sample. FIGS. 6A, 6B and 6C show simplified schematic diagrams of a device 170 with a sample 172 mounted on a sample holder 174 over a mirror 176 where the device 170 is configurable to operate in reflectance (FIG. 6A), transmittance mode (FIG. 6B) and in mixed mode (FIG. 6C), in accordance with an embodiment of the present invention. Sample holder 174 and mirror 176 are coupled to at least one actuator 178 via arms 180 and 182, respectively. Actuator 178, which may be two separate actuators, moves mirror 176 and sample 172 via sample holder 174 to place mirror 176, sample 172, or both mirror 176 and sample 172 within the collection range illustrated by broken lines 184. Of course, if desired, actuator 178 may control only mirror 176 or sample holder 174. Actuator 178 may be any appropriate mechanism that can accurately position sample 172 and/or mirror 176, as is well known in the art.

In another embodiment of the present invention, rather than adjusting the physical location of the sample and/or mirror, the collection range may be altered, e.g., by appropriately adjusting objective lens 154, collection lens 162 and aperture stop 165, shown in FIGS. 3, 4, and 5. Thus, by properly adjusting objective lens 154, collection lens 162 and aperture stop 165 to increase the collection range 158, as is well understood by those skilled in the art, both mirror 160 and sample 156 will be located within the collection range, and metrology device 150 will operate in mixed mode. By decreasing the collection range 158 only mirror 160 or sample 156 will be within the collection range and thus metrology device 150 will operate in transmittance mode or reflectance mode. If desired, both the collection range 158 may be adjusted along with moving the sample and/or mirror as described in reference to FIGS. 6A, 6B, and 6C.

The selectivity of the reflectance mode may be improved by eliminating effects from the mirror 160. Thus, for example, the mirror 160 may be shuttered with a non-reflecting material or with a 45 degree mirror. Alternatively, the mirror 160 may itself be tilted. The selectivity of the transmittance mode may likewise be improved by tilting the sample 156.

Figure 7A:
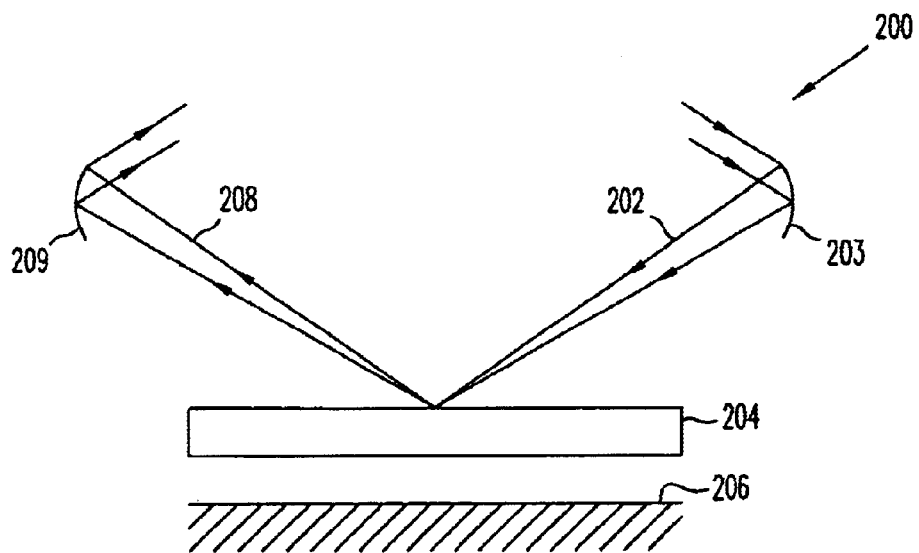
FIGS. 7A and 7B show simplified schematic diagrams of a metrology device in accordance with an embodiment of the present invention in which a beam splitter is not used and the light beam is obliquely incident on the sample.
Figure 7B:
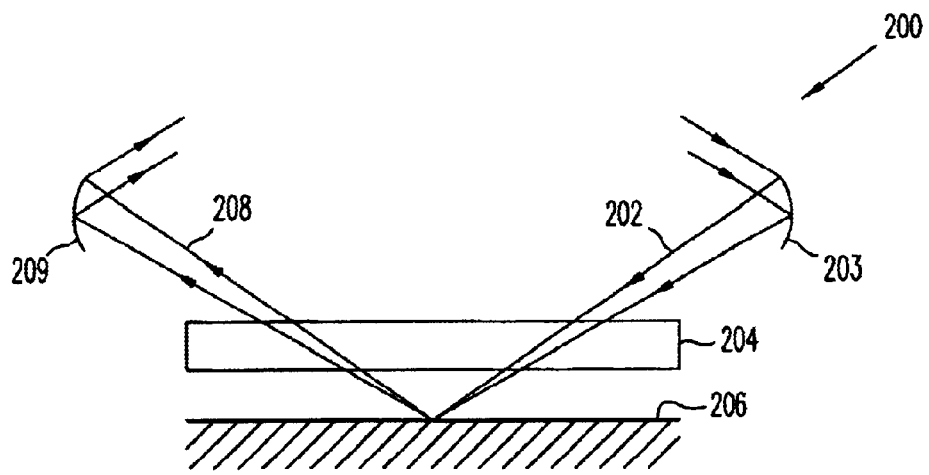

FIGS. 7A and 7B show simplified schematic diagrams of a system 200 in accordance with an embodiment of the present invention in which a beam splitter is not used and the optical path is obliquely incident on sample 204. As shown in FIGS. 7A and 7B, the light beam 202, which has an intensity Io, is focused by mirror 203 to be incident on sample 204 (FIG. 7A) or mirror 206 (FIG. 7B) at an oblique angle. The reflected light beam 208, which has an intensity Is, is received by mirror 209 and reflected to a light detector.

Thus, system 200 may be used in reflectance mode as shown in FIG. 7A or in transmittance mode as shown in FIG. 7B.

Figure 8:
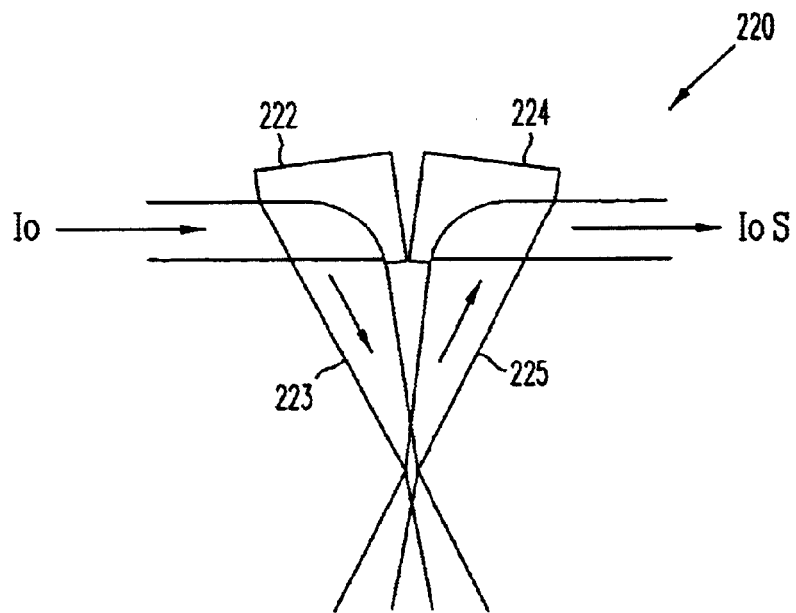
FIG. 8 shows another embodiment of the optical path of a system that may be used in accordance with the present invention.

FIG. 8 shows another embodiment of the optical path of a system 220 that may be used in accordance with the present invention. FIG. 8 is the optical path, e.g., of an FTIR, in which the beam splitter and objective lens are replaced with two parabolic mirrors 222 and 224. In the transmittance mode or the mixed mode, the light beam 223 from parabolic mirror 222 intersects the sample at a slightly different point than the light beam 225 to parabolic mirror 224. As with the system 200 described in reference to FIGS. 7A and 7B, with the emphasis on marginal rays, system 220 will be more binary in its selection between reflectance and transmittance modes. By moving the parabolic mirrors 222 and 224 closer or farther apart and/or masking parts of the surfaces of the parabolic mirrors 222 and 224, the control of the binary selection of system 220, as well as system 200, may be altered.

Although the present invention is illustrated in connection with specific embodiments for instructional purposes, the present invention is not limited thereto. Various adaptations and modifications may be made without departing from the scope of the invention.

What is claimed is:

1. An apparatus for optically measuring characteristics of a sample, said apparatus comprising:
   a light source producing a light beam along an optical path;
   a sample support for holding a sample within said optical path;
   a reflective element within said optical path and downstream of said sample support;
   means for positioning each of a sample held on said sample support, said reflective element, or both said sample held on said sample support and said reflective element within a collection range; and
   a light detector in said optical path, wherein said light detector receives light reflected within said collection range.

2. The apparatus of claim 1, wherein said means for positioning comprises:
   at least one actuator coupled to at least one of said sample support and said reflective element, said at least one actuator moves at least one of said sample support said reflective element upstream and downstream in said optical path.

3. The apparatus of claim 2, wherein said at least one actuator is a first actuator coupled to sample support, said first actuator moves said sample support upstream and downstream in said optical path; and
   a second actuator coupled to said reflective element, said second actuator moves said sample support upstream and downstream in said optical path.

4. The apparatus of claim 1, wherein said means for position comprises:
   lens elements that focus said light beam;
   an aperture stop in said optical path before said light detector, wherein at least one of said lens elements and said aperture stop are adjusted to alter said collection range to position a sample held on said sample support, said reflective element, or both said sample held on said sample support and said reflective element within said collection range.

5. The apparatus of claim 4, wherein said lens elements comprise:
   an objective lens within said optical path before said sample support;
   a collection lens within said optical path after said aperture stop.

6. The apparatus of claim 1, wherein said means for positioning configures said apparatus to operate in one of reflectance mode, transmittance mode, and mixed reflectance and transmittance mode.

7. The apparatus of claim 1, wherein said optical path is at normal incidence to said sample held on said sample support.

8. The apparatus of claim 1, wherein said optical path is at an oblique incidence to said sample on said sample support.

9. The apparatus of claim 1, wherein said means for positioning positions said sample support and said reflective element within said collection range to selectively vary the amount of light received by said light detector that is reflected from said sample held on said sample support and the amount of light that is reflected from said reflective element.

10. An apparatus for optically measuring characteristics of a sample, said apparatus being configurable to operate in one of reflectance mode, transmittance mode, and mixed reflectance and transmittance mode, said apparatus comprising:
    a light source producing a light beam along an optical path;
    a sample support for holding a sample within said optical path;
    a reflective element within said optical path and downstream of said sample support;
    at least one actuator coupled to at least one of said sample support and said reflective element, said at least one actuator moves at least one of said sample support and said reflective element upstream and downstream in said optical path;
    a light detector in said optical path.

11. The apparatus of claim 10, wherein said at least one actuator coupled to at least one of said sample support and said reflective element comprises:
    a first actuator coupled to sample support, said first actuator moves said sample support upstream and downstream in said optical path; and
    a second actuator coupled to said reflective element, said second actuator moves said reflective element upstream and downstream in said optical path.

12. The apparatus of claim 10, wherein said at least one actuator moves at least one of said sample support and said reflective element upstream and downstream in said optical path to selectively vary the amount of reflected light received from said sample and said reflective element.

13. The apparatus of claim 10, wherein said light detector in said optical path receives light reflected from at least one of said sample held on said sample support and said reflective element.

14. An apparatus for optically measuring characteristics of a sample, said apparatus being configurable to operate in one of reflectance mode, transmittance mode, and mixed reflectance and transmittance mode, said apparatus comprising:
    a light source producing a light beam along an optical path;
    a sample support for holding a sample within said optical path;
    a reflective element within said optical path and downstream of said sample support;

lens elements that focus said light beam;

a light detector in said optical path;

an aperture stop in said optical path before said light detector, wherein at least one of said lens elements and said aperture stop are adjusted to alter a collection range to selectively position a sample held on said sample support, said reflective element, or both said sample held on said sample support and said reflective element within said collection range, said light detector detects light reflected within said collection range.

15. The apparatus of claim 14, wherein at least one of said lens elements and said aperture stop are adjusted to selectively vary the amount of light received by said light detector that is reflected from said sample held on said sample support and the amount of light that is reflected from said reflective element.

16. A method of measuring a characteristic of a sample, said method comprising:

producing a light beam to be incident on a sample;

reflecting a portion of said light beam off said sample to form a reflected light beam;

transmitting another portion of said light beam through said sample in a first general direction to form a transmitted light beam;

reflecting said transmitted light beam back toward said sample using a reflective element;

transmitting said transmitted light beam through said sample in a second general direction to form a second transmitted light beam, said second general direction being opposite said first general direction;

selectively configuring a collection range to include said sample, said reflective element or both said sample and said reflective element, said collection range being a range within which light is reflected; and detecting light reflected within said collection range.

17. The method of claim 16, wherein configuring a collection range comprises:

moving said sample to a desired position in or out of said collection range.

18. The method of claim 16, wherein configuring a collection range comprises:

moving a reflective element to a desired position in or out of said collection range, said reflective element being reflects said transmitted light beam back toward said sample.

19. The method of claim 16, wherein configuring a collection range comprises:

adjusting at least one optical element to alter the focus of said light beam between said sample and a reflective element that reflects said transmitted light beam back toward said sample; and adjusting at least one optical element to alter the focus of the light that is detected.

20. The method of claim 16, wherein producing a light beam to be incident on a sample causes said light beam to be normally incident on said sample.

21. The method of claim 16, wherein producing a light beam to be incident on a sample causes said light beam to be obliquely incident on said sample.

22. The method of claim 16, wherein said reflected light beam reflected from said sample is detected.

23. The method of claim 16, wherein said second transmitted light beam is detected.

24. The method of claim 16, wherein both said reflected light beam reflected from said sample and said second transmitted light beam are detected.

25. The method of claim 16, wherein selectively configuring a collection range comprises moving at least one of said collection range, said sample and said reflective element to selectively vary the amount of light received by said light detector that is reflected from said sample and the amount of light that is reflected from said reflective element.

* * * * *